(12) United States Patent
Giovannoni

(10) Patent No.: US 7,723,269 B2
(45) Date of Patent: May 25, 2010

(54) PROCESS FOR SELECTING ANTI-ANGIOGENESIS ANTIBODY FRAGMENTS, ANTI-ANGIOGENESIS ANTIBODY FRAGMENTS THUS OBTAINED AND THEIR USE

(75) Inventor: Leonardo Giovannoni, Siena (IT)

(73) Assignee: Philogen, S.p.A., Siena (IT)

( * ) Notice: Subject to any disclaimer, the term of this patent is extended or adjusted under 35 U.S.C. 154(b) by 426 days.

(21) Appl. No.: 10/450,012

(22) PCT Filed: Dec. 6, 2001

(86) PCT No.: PCT/EP01/14330

§ 371 (c)(1),
(2), (4) Date: Dec. 3, 2003

(87) PCT Pub. No.: WO02/46455

PCT Pub. Date: Jun. 13, 2002

(65) Prior Publication Data

US 2004/0091973 A1    May 13, 2004

(30) Foreign Application Priority Data

Dec. 6, 2000    (IT)    ............................ FI2000A0247

(51) Int. Cl.
*C40B 20/02*    (2006.01)
*C40B 30/04*    (2006.01)
*G01N 33/53*    (2006.01)

(52) U.S. Cl. .................... 506/3; 506/9; 435/7.1

(58) Field of Classification Search .................... 506/3, 506/9; 435/7.1
See application file for complete search history.

(56) References Cited

U.S. PATENT DOCUMENTS 5,565,332 A * 10/1996 Hoogenboom et al. ..... 435/69.1

6,190,660 B1 * 2/2001 Seon ........................ 424/130.1

FOREIGN PATENT DOCUMENTS

| WO | WO 91/05260 | * | 4/1991 |
| WO | WO 97/45544 | * | 12/1997 |
| WO | WO 00/63699 | * | 10/2000 |

OTHER PUBLICATIONS

Viti et al., Design and use of Phage Display Libraries for the Selection of Antibodies and Enzymes, 2000, Methods in Enzymology, pp. 480-505.*
Pini et al., Design and Use of Phage Display Library, 1998, The Journal of Biological Chemistry, 273: 21769-21776.*
Hayes et al., Antivascular therapy: a new approach to cancer treatment., 1999, BMJ (British Medical Journal), 318: 853-856.*
Smith et al., Antibody phage display technologies with special reference to angiogenesis, The FASEB Journal, 19: 331-341, 2005.*
Dreher et al., 1991, Journal of Immunological Methods, 139: 197-205.*
Skerra et al., 1991, Analytical Biochemistry, 196: 151-155.*
Stahl and Uhlen, 1997, Trends Biotechnol, 15(5): 185-192.*
Carnemolla et al., 1996, Phage antibodies with pan-species recognition of the oncofoetal angiogenesis marker fibronectin ED-B domain, Int. J. Cancer, 68: 397-405.*
Giovannoni et al., 2001, Isolation of anti-angiogenesis antibodies from a large combinatorial repertoire by colony filter screening, Nucleic Acids Research, 29: e27 pp. 1-6.*
Winter et al., 1991, Man-made antibodies, Nature, 349: 293-299.*
Tsushita et al., 1996, Phage Display vectors for in vivo recombination of immunoglobulin heavy and light chain genes to make large combinatorial libraries, Gene, 172, 59-63.*
Sudhu, 2001, Engineering M13 for phage display, Biomolecular Engineering, 18: 57-63.*
Pini, A., et al., "Design and use of a phage display library," Journal of Biological Chemistry, 273:21769-21776, (1998).
Borsi, L., et al., "Preparation of phage antibodies to the ED-A domain of human fibronectin," Experimental Cell Research, 240:244-251, (1998).

* cited by examiner

*Primary Examiner*—Amber D. Steele
(74) *Attorney, Agent, or Firm*—Dann, Dorfman, Herrell & Skillman; Kathleen D. Rigaut; Patrick J. Hagan

(57) ABSTRACT

The invention describes a process for filter selection of anti-angiogenesis antibody fragments from a large combinatorial repertoire; the invention further relates to the anti-angiogenesis antibody fragments thus obtained.

6 Claims, 4 Drawing Sheets

PROCESS FOR SELECTING ANTI-ANGIOGENESIS ANTIBODY FRAGMENTS, ANTI-ANGIOGENESIS ANTIBODY FRAGMENTS THUS OBTAINED AND THEIR USE

FIELD OF THE INVENTION

The present invention relates to a process for filter selection of anti-angiogenesis antibody fragments from a large combinatorial repertoir; the invention further relates to the anti-angiogenesis antibody fragments thus obtained.

STATE OF THE ART

As is generally known, functional antibody fragments can be produced in *Escherichia Coli* and displayed on phages, and the processes for selecting antibodies from phage-displayed libraries have now become routine methods allowing to obtain fragments of monoclonal antibodies which can interact practically with any type of antigen in a simple and fast way, at least when the purified antigen is available. It is also known that other techniques allow to avoid the use of phages thanks to the paper selection of antibody fragments secreted by individual bacterial clones. In particular, Skerra et al. [*Anal. Biochem.* 196, 151-155 (1991)] have described a two-membrane system which can determine the bond of an antigen to Fab antibody fragments secreted by bacterial colonies. In short, the method consists in growing bacterial colonies expressing antibodies on a first porous filter and trapping the secreted fragments on another membrane which is then tested for its bond with the antigen. The clones expressing binding antibodies can thus be identified on the first filter and re-grown. However, the method described has been carried out in simple systems consisting of two different binding specificities and starting from few thousands of bacteria, obviously non confluent.

It is obviously quite important to have methods enabling the selection of specific binders starting from large repertoires of antibody fragments expressed in bacteria. As a matter of fact, such methods would allow to avoid the display of antibodies on phages and to identify directly the clones which can express antibody fragments in soluble form.

SUMMARY OF THE INVENTION

The present invention relates to a process in which starting from a highly complex system containing billions of different binding specificities, several cycles of filter selection of colonies and of amplification of positive clones are carried out.

As is evident at this stage, the colonies on the deposit membrane are not confluent anymore, about 30% of the colonies on (A) have produced antibody fragments scFVS which can bind to (B), each of which is therefore a source of anti-ED-B monoclonal antibody fragments.

Figure 1:
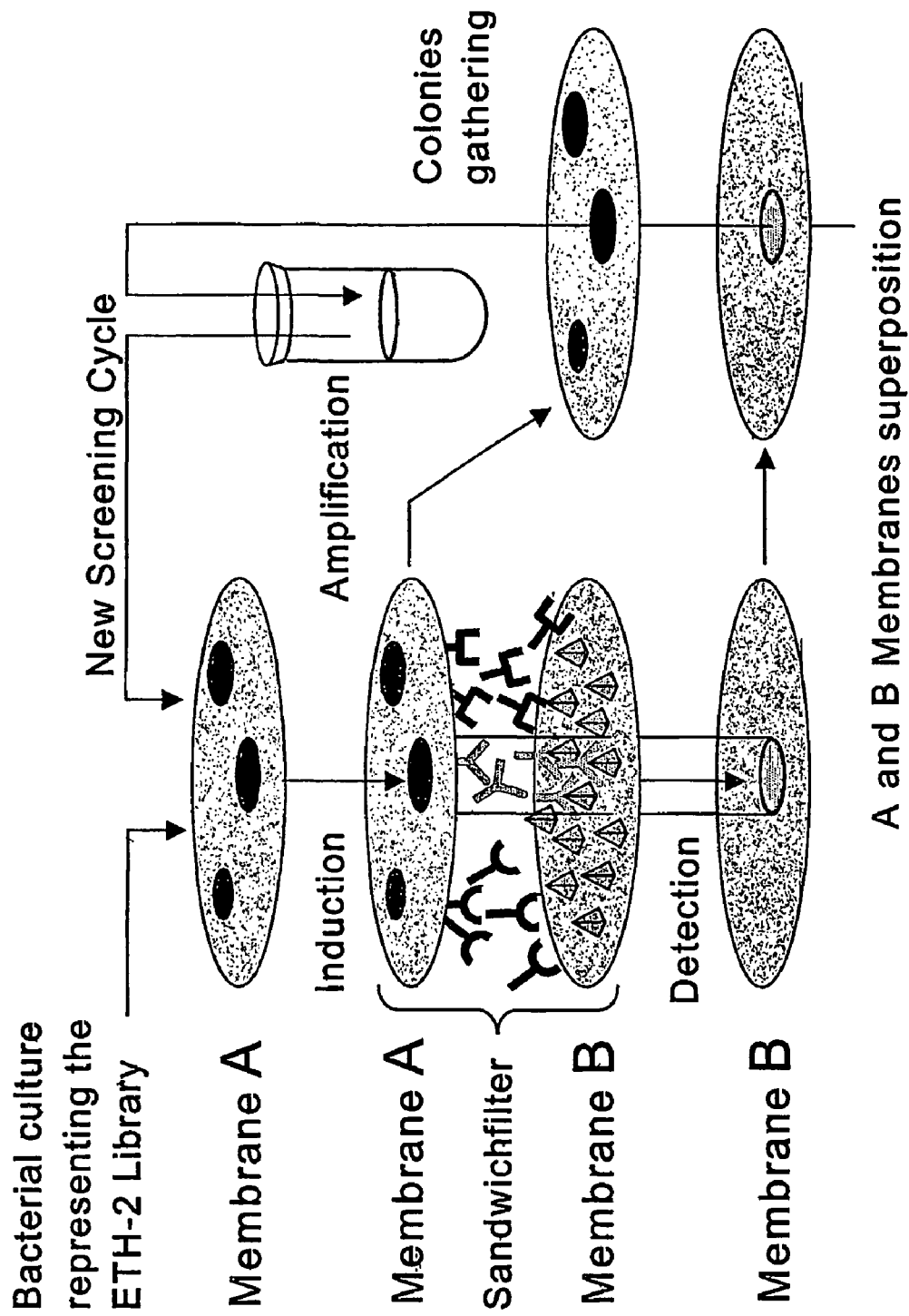
FIG. 1: it shows schematically the method according to the invention as hereinafter described.
Figure 2:
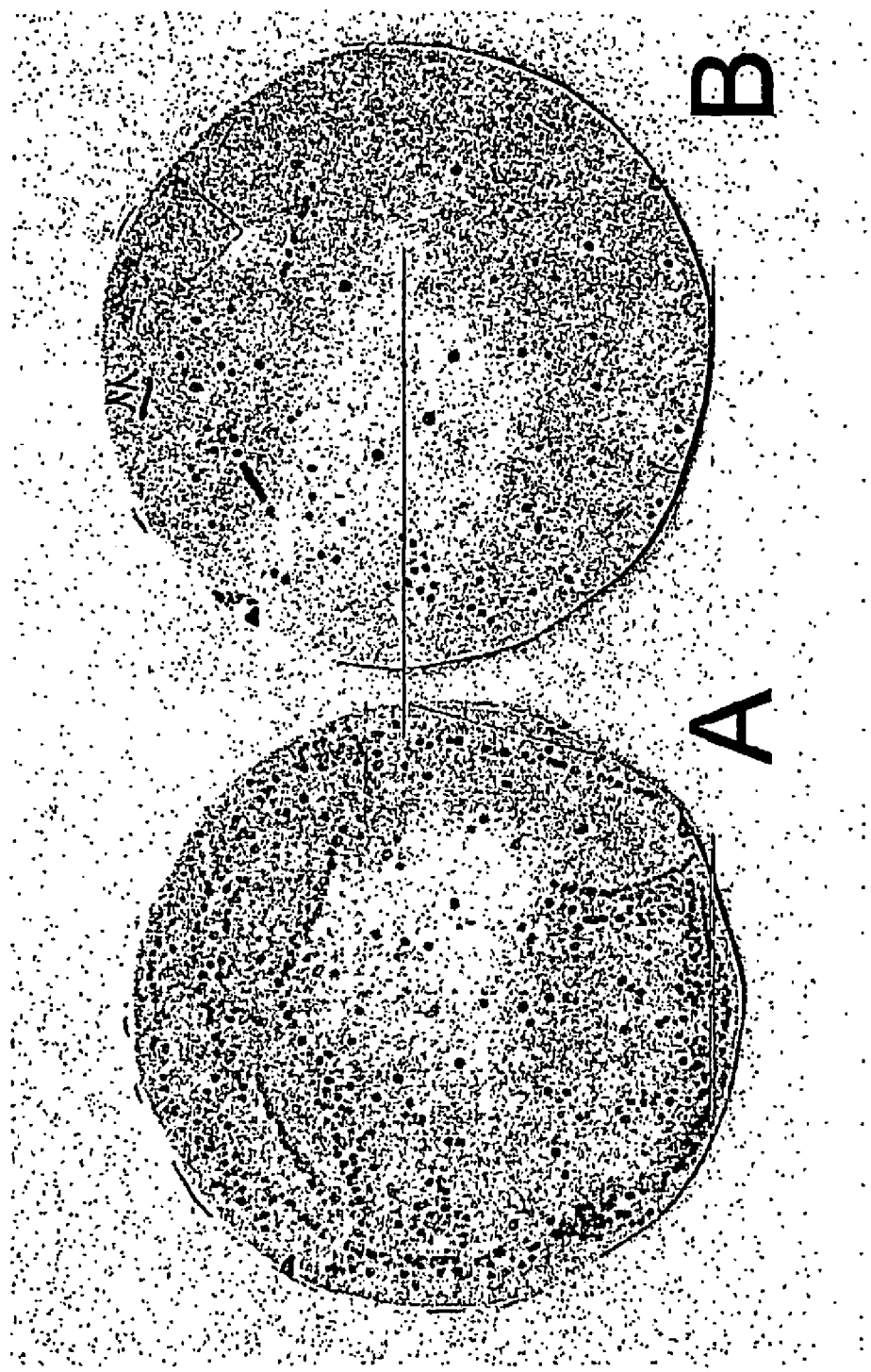
FIG. 2: it shows the deposit membrane (A) and the trap membrane (B) after the development in the third screening cycle of colonies binding to ED-B.
Figure 3:
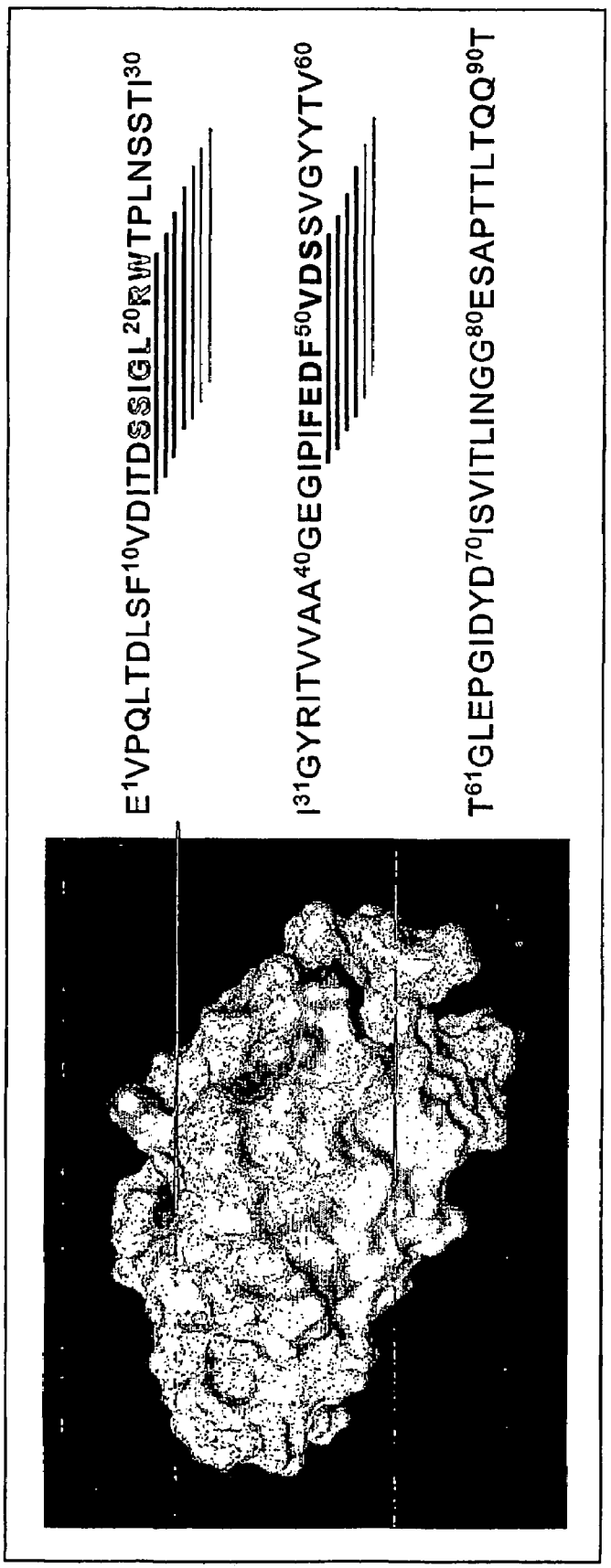

FIG. 3 shows on the right the bond of the antibody ME-4C to each synthetic decapeptide of ED-B sequence and represents it on a horizontal line. The thickness of said line is proportional to the binding affinity observed. Two minimum sequences which have been recognized by the antibodies within the group of synthetic peptides ED-B are highlighted.

Figure 4:
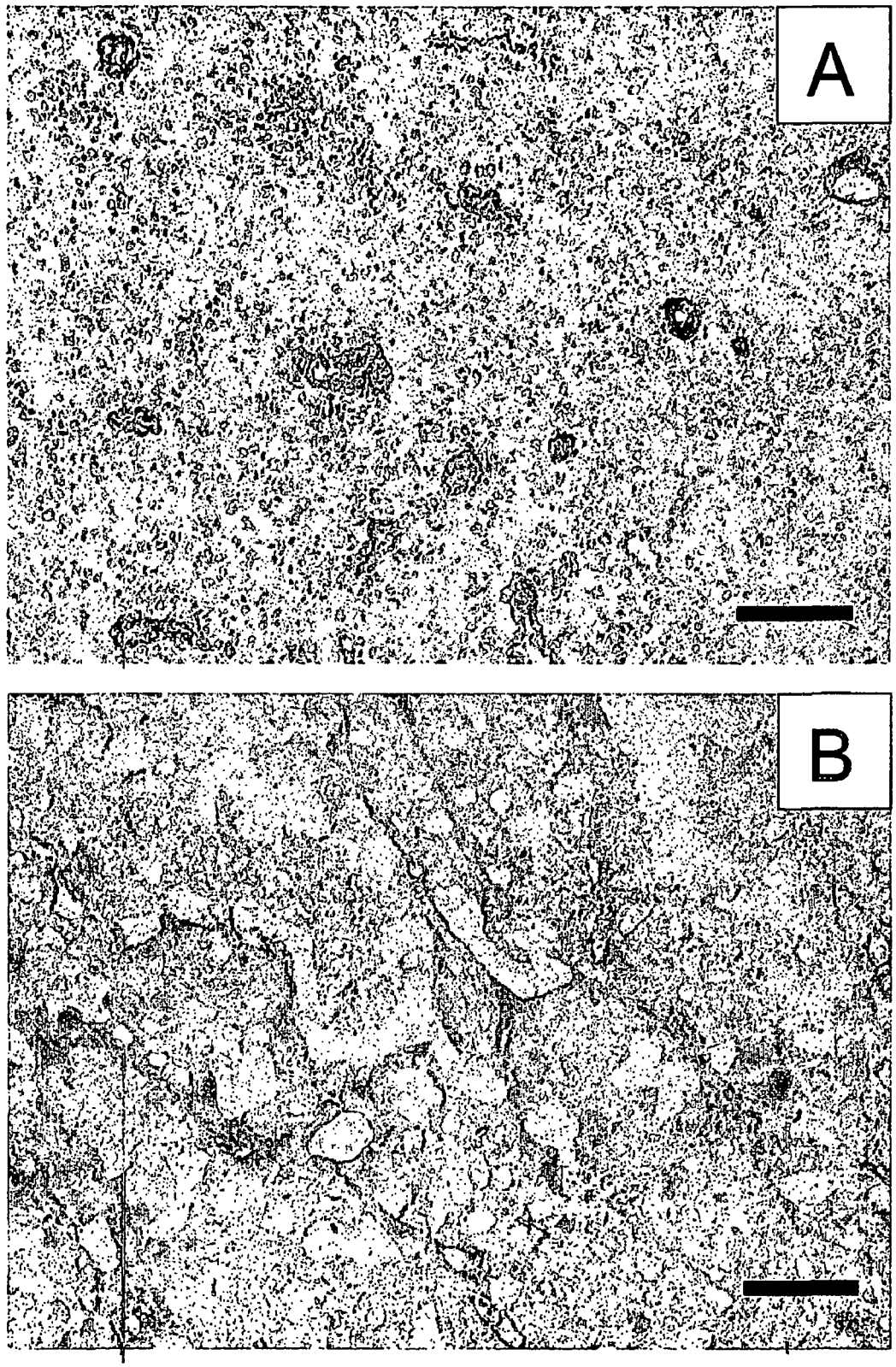

FIG. 4: it summarizes the results of immunohistochemical tests carried out with the antibody fragment scFv ME-4C.

(A) is a section of the sample of a multiform glioblastoma. The typical glomerulus-shaped vascular structures are colored in red by scFv ME-4C.

(B) is a section of human melanoma SKMEL-28 colored with the antibody fragment scFv ME-4C. The antibody places itself around vascular structures and proliferating cells.

DETAILED DESCRIPTION OF THE INVENTION

In the process according to the present invention bacteria containing the DNA encoding several binding specificities are grown in a liquid medium and, once the stage of exponential growth has been reached, some billions of them are distributed onto a growth support consisting of a suitably pre-treated membrane filter which is incubated until completely confluent bacteriae colonies appear.

A second trap substrate consists of another membrane filter, pre-humidified and covered with the desired antgen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped.

The trap membrane is then treated to point out bound antibody fragments scFv with calorimetric techniques commonly used to this purpose.

The position of the colored spots on the trap filter allows to go back to the corresponding bacterial colonies which are present on the growth membrane and produced the antibody fragments trapped.

Such colonies are gathered and grown and the bacteria—a few millions of them—are distributed onto a new culture membrane repeating the procedures described above.

Analogous cycles are then carried out until the positive signals on the trap membrane correspond to single positive colonies, each of which represents a potential source of monoclonal antibody fragments directed against the antigen used in the selection. In particular, the process according to the invention is carried out with bacteria of *E. coli*, strain TG1, hosting DNA encoding the various binding specificities and containing ETH-2library [described in Viti et al., *Methods ni Enzymology*, 326, 480-505]. As trap antigen the recombinant protein 7B89 has been chosen [Castellani et al. (1994) *Int. J. Canc.* 59, 612-618] containing the domains 7, ED-B, 8, 9 of Fibronectin.

By operating as described above the clones obtained at the end of the third cycle are grown and produce soluble fragments of antibody fragments scFvs.

In particular, one of the monoclonal antibody fragments (hereinafter identified as ME-4C) is isolated and sequenced thanks to its capacity of binding to ED-B of Fibronectin. ME-4C binds to ED-B with an affinity in the order of nanomoles according to the data obtained for antibody fragments previously selected from the same repertoir.

Experimental Section

ETH-2 Library

This is a phage-display library of recombinant antibody fragments scFv containing more than $5 \times 10^8$ individual clones. The diversity is introduced into the antibodies in the Complementarity Determining Region 3 (CDR-3) both of the Variable Heavy (VH) chain and of the Variable Light (VL) chain. The genes encoding VH and VL are cloned in a vector enabling their expression in soluble form. Moreover, said vector introduces an identification on the carboxylic terminal of antibody fragments scFv.

Growth of the Colony and Expression of Antibody Fragments scFv

ETH-2 library is kept as bacteria (*E.coli*, strain TG1) hosting the DNA encoding the various specificities. Said bacteria are grown in a liquid medium and once they have reached the stage of exponential growth $10^8$, they are distributed on a Durapore membrane filter in PVDF with a diameter of 20 cm (type GVWP, Millipore). Said filter is placed in a Petri plate with a diameter of 20 cm, containing TYE Agar (Miller, 1972), 100 µg/ml of Ampicillin, 1% of glucose, and incubated at 37° C. for 8 h. After the incubation completely confluent bacteriae colonies can be seen on the filter. A second (trap) membrane is prepared by pre-humidifying a membrane with a diameter of 20 cm in PVDF (Immobilon-P, Millipore) and covering it with the trap antigen. As trap antigen the recombinant protein 7B89 containing domains 7, ED-B, 8, 9 of Fibronectin is chosen. The recombinant domain ED-B of Fibronectin alone, i.e. our target for antibody isolation, does not bind to the membrane. The covering of the membrane is obtained by incubating said membrane at 37° C. for 6 h in a solution of 50 mM phosphate, pH 7.4, 100 mM NaCl (phosphate buffer, PBS) containing 150 µg/ml of 7B89. The filter is then blocked in a 5% solution milk/PBS (MPBS) at 37° C. for 2 h, washed 4 times in 0.2% PBS (v/v) Tween 20 (PBST) and Immersed in 2xTY containing 100 µg/ml of Ampicillin and 1 mM isopropyl-β-D-thiogalactopyranoside (IPTG).

The trap membrane is placed on a plate of TYE Agar containing 100 µg/ml of Ampicillin and 1 mM of IPTG and covered with Durapore membrane with the bacterial colonies pointing upwards.

The sandwich structure thus obtained is incubated at room temperature for 16 hours. The presence of IPTG in the medium together with the absence of glucose enables the expression (regulated by Lac promoter) of the genes encoding antibody fragments scFvs having a spreading action, those specifically binding for protein 7B89 being thus trapped by the second membrane.

Detection of the Bond With the Antigen

The trap membrane is washed four times with PBST and blocked in MPBS at 37° C. for 6 h. In order to determine the bound antibody fragments scFv, the filter is incubated with anti-flag M2 murine antibody (Sigma, F-3165) diluted 1:3000 in MBST at 37° C. for 1 h, washed 4 times in PBST and incubated with Horseradish Peroxidase (HRP) conjugated with anti-mouse rabbit IgG (bioRad, 172-1011) diluted 1:3000 in MBST at 37° C. for 1 h. The filter is then abundantly washed with PBST and incubated in 4-chloro-1-naphthol until dark spots are observed. The enzymatic colorimetric reaction is interrupted by washing with water and the filter is then dried.

The alignment signs obtained by placing the two filter one onto the other allows to go back from the colored spots on the trap filter to the producing bacterial colony of the first filter.

Amplification of Positive Clones

After the first screening cycle the positive signals on the trap filter correspond to the areas of confluent bacteriae colonies on the first filter which have been gathered and grown in 2xTY, 100 µg/ml of Ampicillin, 1% (w/v) of glucose up to O.D. (600 nm)=0.7.

At this stage $10^6$ bacteria are distributed onto a new Durapore membrane and the processes described above are repeated. At the end of the second cycle the positive signals correspond to monocoalescent colonies. 18 of these colonies are picked up, grown and used for a successive screening in which $5 \times 10^3$ bacteria are placed on the Durapore filter. After the third cycle the positive signals on the trap membrane correspond to single positive colonies, each of which represents a source of monoclonal antibodies directed against antigen 7B89.

Characterization of Selected Antibodies

Individual positive clones obtained after the third screening cycle as described above are grown in a liquid medium and produce soluble fragments of antibody fragments scFvs. The binding specificity of these fragments is then determined with an ELISA test carried out on ED-B, 7B89 or irrelevant antigens (MPBS, BSA, Ovalbumin, Lysoenzyme).

The kinetic coefficients concerning association and dissociation of antibody fragments are determined by plasma surface resonance with BIAcore 1000 (Pharmacia) following known protocols. Few clones which were positive to the ELISA test are chosen for the measurements. The measurements are carried out with the monomer fraction of antibody fragments scFvs as described in relevant documents, using chips covered both with ED-B and with 7B89.

Clone sequencing is carried out with a DNA sequencer 377 ABI Prism (Perkin-Elmer). The epitopes on ED-B recognized by one of the antibody fragments scFvs selected (hereinafter defined as ME-4C) are identified using the SPOT synthesis method as described for other anti-ED-B antibody fragments.

Immunohistochemistry

The immunocoloring of sections of multiform glioblastoma and human melanoma SK-MEL is carried out as known in the corresponding scientific literature.

In order to identify whether the antibody isolated from the library with the process described above had a good affinity towards the native antigen, a real-time interaction analysis is applied using plasma surface resonance with a BIAcore device. The monomer fraction of ME-4C binds to ED-B with an affinity of $10^{-7}$ M$^{-1}$ with a kinetic dissociation constant ($K_{off}$) of $6 \times 10^{-3}$ s$^{-1}$ and a kinetic association constant ($K_{on}$) of $6 \times 10^4$ s$^{-1}$ M$^{-1}$.

In order to further characterize the bond between the antibody fragment ME-4C and ED-B, the epitopes recognized by the antibody fragment scFv are identified using the SPOT synthesis method. A series of 82 decapeptides covering the sequences of the 91 ED-B residues is tested for its bond with ME-4C.

In order to determine whether the selected antibody fragment scFv ME-4C could act as reagent in the identification of angiogenesis in tissue samples, studies are carried out on tumor sections: the results are summarized in FIG. 4.

As shown by immunohistochemical experiments carried out on sections of human multiform glioblastoma and melanoma, the antibody ME-4C can mark blood vessels building up in tumor tissues, which makes said antibody a valuable help for clinical applications such as the analysis of tissue sections for the angiogenesis determination.

The invention claimed is:

1. A process for selecting anti-angiogenesis antibody fragments comprising:
(i) distributing bacterial colonies expressing billions of different binding specificities in soluble form onto a growth filter, wherein all of said bacterial colonies are grown until completely confluent and are present on said growth filter and said binding specificities comprise antibody fragments;
(ii) incubating the growth filter until the colonies are confluent;
(iii) providing a trap filter comprising a trapped antigen;
(iv) placing the trap filter in a plate containing culture medium;
(v) covering the trap filter with the growth filter with the bacterial colonies pointing upwards;
(vi) incubating the growth filter and the trap filters, such that antibody fragments expressed by the colonies on the growth filter bind to the antigen on the trap filter;
(vii) detecting the binding of antibody fragments to the trap filter;
(viii) identifying the bacterial colonies on the growth filter which expressed the antibody fragments bound to the trap filter;
(viii) identifying the bacterial colonies on the growth filter which expressed the antibody fragments bound to the trap filter, while avoiding the display of antibodies on phage
(ix) growing the identified bacterial colonies in liquid medium;
(x) distributing said identified bacterial colonies onto a membrane filter; and
(xi) repeating steps (iii) to (x) for additional cycles until single colonies expressing antibody fragments which bind to the trap filter are identified in step (viii), said single colonies producing soluble anti-angiogenesis antibody fragments.

2. The process of claim 1 wherein the desired antigen is the ED-B of fibronectin.

3. The process of claim 1 wherein said anti-angiogenesis fragment is a scFv.

4. The process of claim 3 further comprising the method step of screening the scFv for binding to blood vessels thereby marking the blood vessels.

5. The process of claim 1, wherein at least three cycles are carried out.

6. The process of claim 5, wherein:
the colonies of step (i) are *E. coli* bacteria strain TG1 comprising a DNA scFv library encoding the various binding specificities which are distributed onto said growth filter;
the antigen of step (iii) is 7B89 containing the domains 7, ED-B, 8, 9 of Fibronectin;
the trap filter of step of step (v) is placed in a plate containing culture medium and covered with the growth filter with the bacterial colonies pointing upwards;
detection of positive signals of step (vii) due to bonding of scFvs on the trap filter is via colorimetric reactions;
positions of the signals identified in step (viii) are compared with the colonies which are present on the growth filter by picking up the colony areas corresponding to said signals thereby identifying said colonies;
the colonies gathered in step (ix) undergo two further analogous growth and identification cycles:
the single colonies identified in step (xi) are picked up from the second of the said two further cycles; and
the scFvs produced thereby are isolated.

* * * * *

SEQUENCE LISTING

<160> NUMBER OF SEQ ID NOS: 5

<210> SEQ ID NO 1
<211> LENGTH: 720
<212> TYPE: DNA
<213> ORGANISM: Homo Sapiens
<220> FEATURE:
<221> NAME/KEY: CDS
<222> LOCATION: (1)...(720)
<223> OTHER INFORMATION: nucleotide sequence corresponding to scFv ME-4C

<400> SEQUENCE: 1

| gag gtg cag ctg gtg gag tct ggg gga ggc ttg gta cag cct ggg ggg | 48 |
|---|---|
| Glu Val Gln Leu Val Glu Ser Gly Gly Gly Leu Val Gln Pro Gly Gly | |
| 1               5                   10                  15 | |

| tcc ctg aga ctc tcc tgt gca gcc tct gga ttc acc ttt agc agc tat | 96 |
|---|---|
| Ser Leu Arg Leu Ser Cys Ala Ala Ser Gly Phe Thr Phe Ser Ser Tyr | |
|             20                  25                  30 | |

| gcc atg agc tgg gtc cgc cag gct cca ggg aag ggg ctg gag tgg gtc | 144 |
|---|---|
| Ala Met Ser Trp Val Arg Gln Ala Pro Gly Lys Gly Leu Glu Trp Val | |
|         35                  40                  45 | |

| tca gct att agt ggt agt ggt ggt agc aca tac tac gca gac tcc gtg | 192 |
|---|---|
| Ser Ala Ile Ser Gly Ser Gly Gly Ser Thr Tyr Tyr Ala Asp Ser Val | |
|     50                  55                  60 | |

| aag ggc cgg ttc acc atc tcc aga gac aat tcc aag aac acg ctg tat | 240 |
|---|---|
| Lys Gly Arg Phe Thr Ile Ser Arg Asp Asn Ser Lys Asn Thr Leu Tyr | |
| 65                  70                  75                  80 | |

| ctg caa atg aac agc ctg aga gcc gag gac acg gcc gta tat tac tgt | 288 |
|---|---|
| Leu Gln Met Asn Ser Leu Arg Ala Glu Asp Thr Ala Val Tyr Tyr Cys | |
|             85                  90                  95 | |

| gcg aaa cag aag agt gcg ccg ttt gac tac tgg ggc cag gga acc ctg | 336 |
|---|---|
| Ala Lys Gln Lys Ser Ala Pro Phe Asp Tyr Trp Gly Gln Gly Thr Leu | |
|         100                 105                 110 | |

| gtc acc gtg tcg aga ggt gga ggc ggt tca ggc gga ggt ggc tct ggc | 384 |
|---|---|
| Val Thr Val Ser Arg Gly Gly Gly Gly Ser Gly Gly Gly Gly Ser Gly | |
|     115                 120                 125 | |

| ggt ggc gga tcg tct gag ctg act cag gac cct gct gtg tct gtg gcc | 432 |
|---|---|
| Gly Gly Gly Ser Ser Glu Leu Thr Gln Asp Pro Ala Val Ser Val Ala | |
| 130                 135                 140 | |

| ttg gga cag aca gtc agg atc aca tgc caa gga gac agc ctc aga agc | 480 |
|---|---|
| Leu Gly Gln Thr Val Arg Ile Thr Cys Gln Gly Asp Ser Leu Arg Ser | |
| 145                 150                 155                 160 | |

| tat tat gca agc tgg tac cag cag aag cca gga cag gcc cct gta ctt | 528 |
|---|---|
| Tyr Tyr Ala Ser Trp Tyr Gln Gln Lys Pro Gly Gln Ala Pro Val Leu | |
|             165                 170                 175 | |

| gtc atc tat ggt aaa aac aac cgg ccc tca ggg atc cca gac cga ttc | 576 |
|---|---|
| Val Ile Tyr Gly Lys Asn Asn Arg Pro Ser Gly Ile Pro Asp Arg Phe | |
|         180                 185                 190 | |

| tct ggc tcc agc tca gga aac aca gct tcc ttg acc atc act ggg gct | 624 |
|---|---|
| Ser Gly Ser Ser Ser Gly Asn Thr Ala Ser Leu Thr Ile Thr Gly Ala | |
|     195                 200                 205 | |

| cag gcg gaa gat gag gct gac tat tac tgt aac tcc tct gcg ccc gtt | 672 |
|---|---|
| Gln Ala Glu Asp Glu Ala Asp Tyr Tyr Cys Asn Ser Ser Ala Pro Val | |
| 210                 215                 220 | |

| agt aat agg gtg gta ttc ggc gga ggg acc aag ctg acc gtc cta ggc | 720 |
|---|---|
| Ser Asn Arg Val Val Phe Gly Gly Gly Thr Lys Leu Thr Val Leu Gly | |
| 225                 230                 235                 240 | |

<210> SEQ ID NO 2
<211> LENGTH: 240

```
<212> TYPE: PRT
<213> ORGANISM: Homo Sapiens

<400> SEQUENCE: 2

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Lys Ser Ala Pro Phe Asp Tyr Trp Gly Gln Gly Thr Leu
            100                 105                 110

Val Thr Val Ser Arg Gly Gly Gly Gly Ser Gly Gly Gly Gly Ser Gly
        115                 120                 125

Gly Gly Gly Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Ala Pro Val
    210                 215                 220

Ser Asn Arg Val Val Phe Gly Gly Gly Thr Lys Leu Thr Val Leu Gly
225                 230                 235                 240

<210> SEQ ID NO 3
<211> LENGTH: 8
<212> TYPE: PRT
<213> ORGANISM: Homo Sapiens
<220> FEATURE:
<221> NAME/KEY: DOMAIN
<222> LOCATION: (1)...(8)
<223> OTHER INFORMATION: region corresponding to the CDR3 of ME-4C scFv
      heavy chain

<400> SEQUENCE: 3

Tyr Cys Ala Gln Lys Ser Ala Pro
  1               5

<210> SEQ ID NO 4
<211> LENGTH: 10
<212> TYPE: PRT
<213> ORGANISM: Homo Sapiens
<220> FEATURE:
<221> NAME/KEY: DOMAIN
<222> LOCATION: (1)...(10)
<223> OTHER INFORMATION: region corresponding to CDR3 of ME-4C scFv
      light chain

<400> SEQUENCE: 4
```

-continued

```
Ser Ser Ala Pro Val Ser Asn Arg Val Val
1               5                   10

<210> SEQ ID NO 5
<211> LENGTH: 91
<212> TYPE: PRT
<213> ORGANISM: Homo Sapiens

<400> SEQUENCE: 5

Glu Val Pro Gln Leu Thr Asp Leu Ser Phe Val Asp Ile Thr Asp Ser
1               5                   10                  15

Ser Ile Gly Leu Arg Trp Thr Pro Leu Asn Ser Ser Thr Ile Ile Gly
            20                  25                  30

Tyr Arg Ile Thr Val Val Ala Ala Gly Glu Gly Ile Pro Ile Phe Glu
        35                  40                  45

Asp Phe Val Asp Ser Ser Val Gly Tyr Tyr Thr Val Thr Gly Leu Glu
    50                  55                  60

Pro Gly Ile Asp Tyr Asp Ile Ser Val Ile Thr Leu Ile Asn Gly Gly
65                  70                  75                  80

Glu Ser Ala Pro Thr Thr Leu Thr Gln Gln Thr
                85                  90
```